(12) United States Patent
Park et al.

(10) Patent No.: US 11,604,177 B1
(45) Date of Patent: Mar. 14, 2023

(54) SMART TOILET FOR HUMAN HEALTH MONITORING

(71) Applicant: THE BOARD OF TRUSTEES OF THE LELAND STANFORD JUNIOR UNIVERSITY, Stanford, CA (US)

(72) Inventors: Seung-Min Park, Menlo Park, CA (US); Daeyoun Won, Seoul (KR); Brian J. Lee, Mountain View, CA (US); Sunil Bodapati, Saratoga, CA (US); Alexander Lozano, Stanford, CA (US); Diego Escobedo, Burlingame, CA (US); Sanjiv Sam Gambhir, Portola Valley, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 747 days.

(21) Appl. No.: 16/506,942

(22) Filed: Jul. 9, 2019

Related U.S. Application Data

(60) Provisional application No. 62/796,875, filed on Jan. 25, 2019, provisional application No. 62/695,326, filed on Jul. 9, 2018.

(51) Int. Cl.
*G01N 31/22* (2006.01)
*A47K 17/00* (2006.01)
(Continued)

(52) U.S. Cl.
CPC .............. *G01N 31/22* (2013.01); *A47K 17/00* (2013.01); *A61B 5/0077* (2013.01);
(Continued)

(58) Field of Classification Search
CPC ...... G01N 31/22; A47K 17/00; A61B 5/0077; A61B 5/1171; A61B 5/1172;
(Continued)

(56) References Cited

U.S. PATENT DOCUMENTS 9,428,898 B1 * 8/2016 Clements .................. E03D 9/08
9,477,317 B1 * 10/2016 Clements ................ G06F 3/017
(Continued)

FOREIGN PATENT DOCUMENTS

WO WO-2016135735 A1 * 9/2016 ......... A61B 10/0038
WO WO-2017021452 A1 * 2/2017 ......... A61B 10/0012

*Primary Examiner* — Jennifer Wecker
*Assistant Examiner* — Alea N. Martin
(74) *Attorney, Agent, or Firm* — KPPB LLP

(57) ABSTRACT

Devices, systems, and methods are provided for monitoring or analyzing excreta of a subject using a toilet. In one embodiment, the device includes a housing mounted adjacent a toilet bowl, a urinalysis module for deploying urinalysis strips into the toilet bowl to collect a urine sample from a subject's urine stream delivered into the toilet bowl and a urinalysis sensor to acquire data from the urinalysis strip related to the urine sample, and a stool analysis module including a camera oriented into the toilet bowl to provide images of contents of the toilet bowl. In addition, the device may include a uroflowmetry module and/or a biometric identification module. One or more sensors are provided for identifying when a subject uses the toilet, and a processor activates one or more of the modules when the sensors indicate a subject is using the toilet.

22 Claims, 10 Drawing Sheets

(51) Int. Cl.
  *A61B 10/00* (2006.01)
  *A61B 5/1171* (2016.01)
  *A61B 5/1172* (2016.01)
  *G06T 7/00* (2017.01)
  *G06T 7/90* (2017.01)
  *G06T 7/20* (2017.01)
  *A61B 5/00* (2006.01)

(52) U.S. Cl.
  CPC .......... *A61B 5/1171* (2016.02); *A61B 5/1172* (2013.01); *A61B 10/007* (2013.01); *G06T 7/0012* (2013.01); *G06T 7/20* (2013.01); *G06T 7/90* (2017.01); *G06T 2207/10024* (2013.01); *G06T 2207/30004* (2013.01)

(58) Field of Classification Search
  CPC ....... A61B 10/007; G06T 7/0012; G06T 7/20; G06T 7/90; G06T 2207/10024; G06T 2207/30004
  See application file for complete search history.

(56) References Cited

U.S. PATENT DOCUMENTS

| | | | |
|---|---|---|---|
| 10,376,246 B2 | 8/2019 | Kashyap et al. | |
| 2014/0147924 A1* | 5/2014 | Wheeldon | G01N 21/76 436/63 |
| 2014/0323836 A1* | 10/2014 | Kusukame | A61B 5/6891 600/300 |
| 2019/0293636 A1* | 9/2019 | Tsuruoka | G16H 10/40 |

* cited by examiner

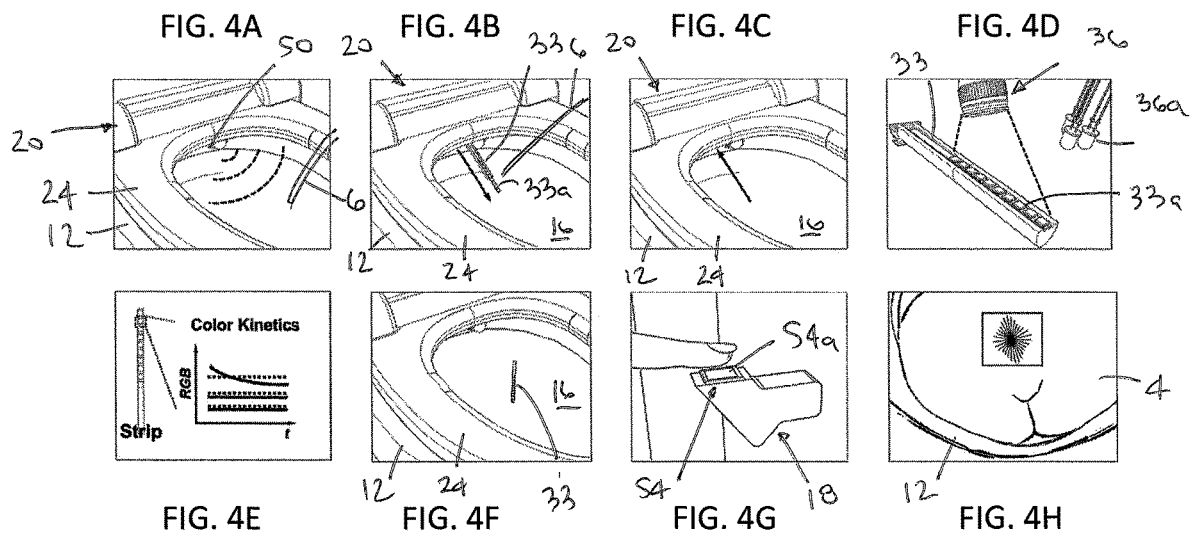
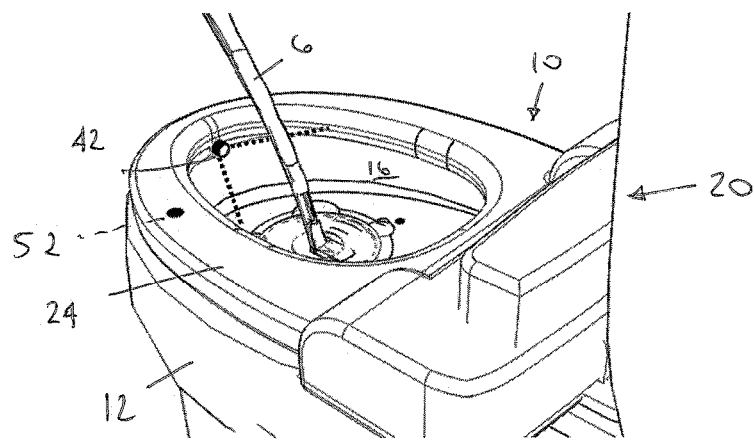
FIG. 5A
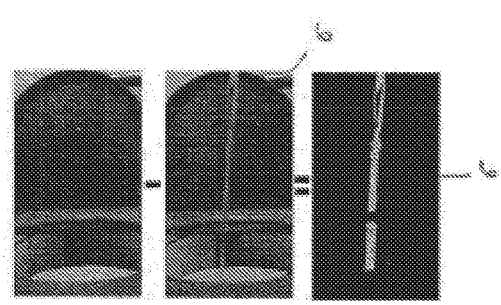

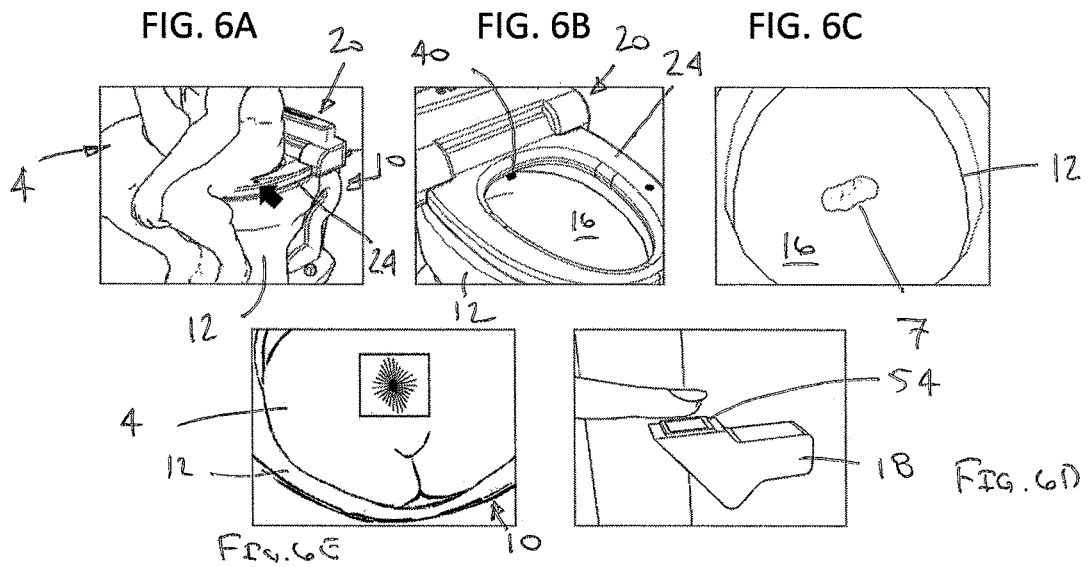
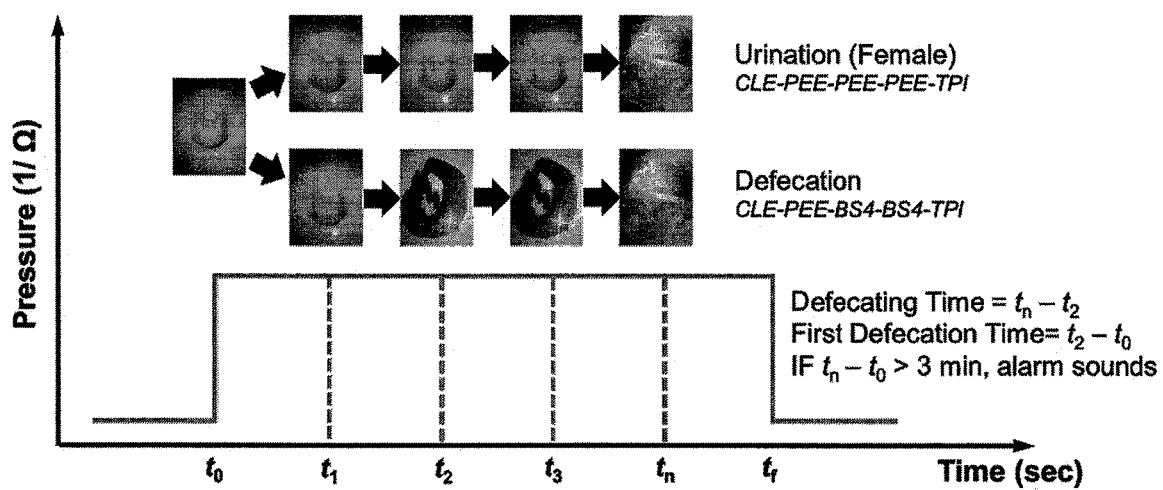
FIG. 7

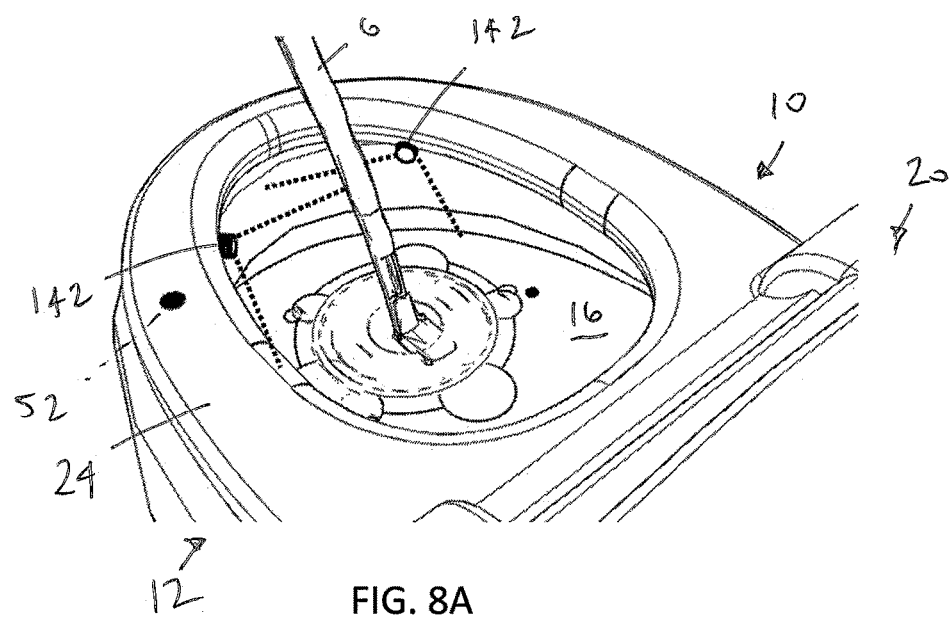
FIG. 8A
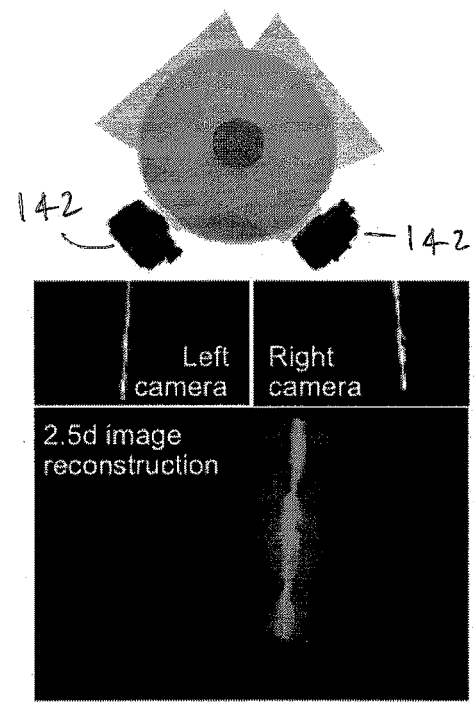
FIG. 8B
FIG. 8C

FIG. 10
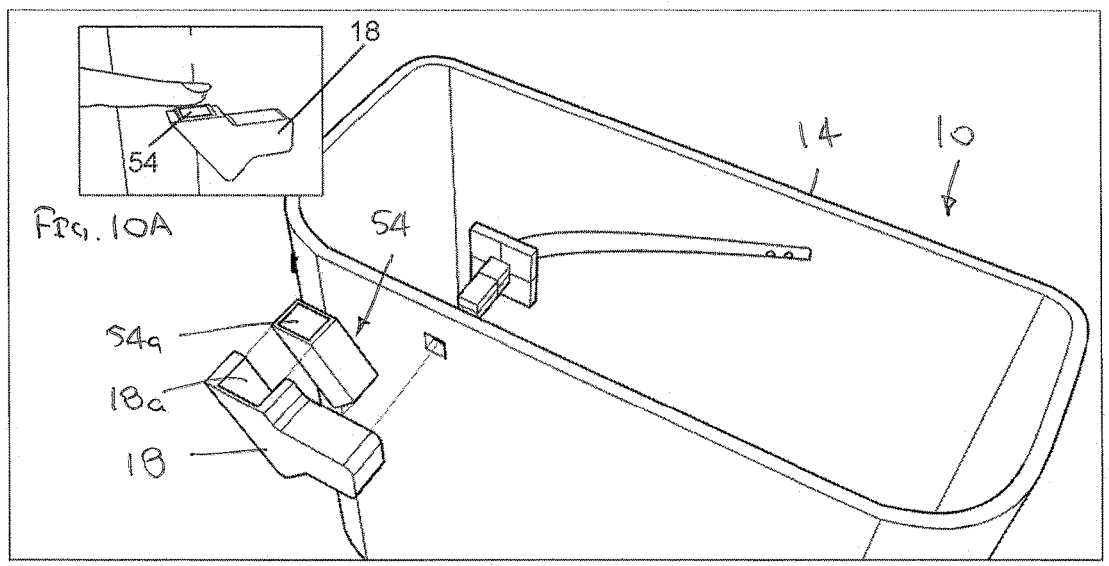
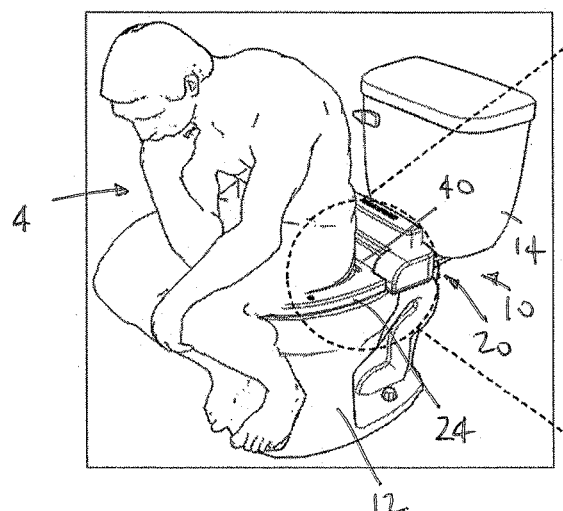
FIG. 11A
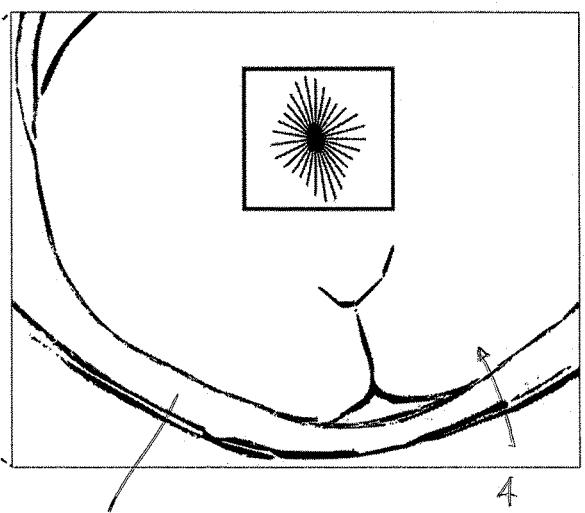
FIG. 11B

|  | Description | |
|---|---|---|
| Type 1 | "Separate hard lumps, like nuts (hard to pass)" |  |
| Type 2 | "Sausage-shaped but lumpy" |  |
| Type 3 | "Like a sausage but with cracks on the surface" |  |
| Type 4 | "Like a sausage or snake, smooth and soft" |  |
| Type 5 | "Soft blobs with clear cut edges (passed easily)" |  |
| Type 6 | "Fluffy pieces with ragged edges, a mushy stool" |  |
| Type 7 | "Watery, no solid pieces, entirely liquid" |  |
FIG. 14

SMART TOILET FOR HUMAN HEALTH MONITORING

RELATED APPLICATION DATA

The present application claims benefit of co-pending U.S. provisional applications Ser. Nos. 62/695,326, filed Jul. 9, 2018 and 62/796,875, filed Jan. 26, 2019, the entire disclosures of which are expressly incorporated by reference herein.

FIELD OF THE INVENTION

The present invention relates generally to health monitoring devices, systems, and methods and, more particularly, to systems and methods for monitoring and/or analyzing a subject during urination and/or defecation, e.g., to devices and systems that may be added to a toilet or integral smart toilets that monitor and/or analyze the subject's excreta, e.g., urine and/or stools, during urination and/or defecation.

BACKGROUND

The early detection and treatment of diseases can result in an improved prognosis and increased quality of life. To detect various diseases including cancer, diabetes, and renal disease early, it is desirable to establish a platform capable of routinely monitoring human health, e.g., to establish a patient-specific baseline for diagnostic biomarkers. Having established a baseline, detecting trends may allow physicians to warn users that they might be developing an illness. Unfortunately, patients have biomarkers measured irregularly, usually when they are already experiencing symptoms, which may hamper the ability of physicians to establish reliable baselines.

Invasive procedures such as surgery and X-ray imaging are not the best options for continuous monitoring since they are costly and can be burdensome for the general population. Sources of diagnostic information include the molecular contents of sweat, saliva, urine, and feces, all of which are naturally excreted every day and packed with information. Much research has indicated that these substances can provide clues to our health and can be continuously obtained through the development of appropriate diagnostic tools.

Therefore, systems and methods for monitoring a subject's health would be useful.

SUMMARY

The present invention is directed to health monitoring devices, systems, and methods, and, more particularly, to systems and methods for monitoring and/or analyzing a subject during urination and/or defecation. More particularly, the present invention is directed to devices and systems that may be added to a toilet or integral toilet systems that monitor and/or analyze the subject's excreta, e.g., urine and/or stools, during urination and/or defecation, and to methods for using such devices and systems.

The devices herein may be mounted on or integrated into a toilet, and automatically monitor and/or inspect a subject's excreta, e.g., to inspect for the presence of markers in the excreta voided by the users of the devices. The devices may be configured to not interfere with normal human behavior using the toilet and may include one or more of automatic user identification, excretion detection, and/or analysis features, as described elsewhere herein.

In particular, the devices may allow autonomous and/or substantially continuous individualized monitoring of excreted waste from one or more subjects or users, e.g., to establish health baselines and/or monitor trends or changes. The devices may overcome issues of sporadic data collection by using automatic urine and/or stool detection, recovery, and analysis technology, which may provide a plurality of data points, e.g., six or seven data points per individual every day, which may enhance detection of various health conditions or events.

In an exemplary embodiment, a device and system may be provided that may substantially continuously monitor and/or analyze excreta to provide urine analysis, e.g., one or both of urinalysis/uroflowmetry, and stool analysis. For example, the device may include a urinalysis module including urinalysis strips that may be fed from a disposable cartridge to a movable stage, which may be deployed into the toilet bowl and into the stream of urine to collect a sample, which the device may then analyze. The urinalysis strips may be composed of a water-soluble backbone and/or other material, which enable disposal of the used strip into the toilet after analysis. In addition, the device may include one or more cameras configured to provide video analysis of urine streams, e.g., using uroflowmetry to measure baselines and/or identify abnormal urine flow associated with diseases. In addition, the device may include a stool analysis module including a camera, which may acquire images of stool in the toilet for analysis, e.g., for grading on the Bristol Stool Form Scale (BSFS), using an automated classifier using a machine-learning algorithm, and/or acquire images of discarded toilet paper, e.g., to identify colorimetric, fecal occult blood, and/or other changes for screening cancer and/or other conditions.

Optionally, the stool analysis module may monitor and/or analyze additional information, such as time to first stool, total seating time, actual defecating time and/or other parameters of the subject, which may potentially be acted on by clinicians to help manage constipation, hemorrhoids, and/or other conditions. In addition or alternatively, the device may include one or more components to identify one or more biometric identifiers of individual subjects using the toilet, e.g., to distinguish and monitor multiple subjects, such as a fingerprint reader and/or a camera system for acquiring anal prints (anus wrinkle) of subjects using the toilet, which may facilitate securely associating collected data with each subject.

In accordance with one embodiment, a device is provided for monitoring or analyzing excreta of a subject using a toilet that includes a housing mountable on a toilet adjacent the toilet bowl; a cartridge comprising one or more urinalysis strips within the housing; a sensor for identifying when a subject begins using the toilet; an actuator configured to direct a first end of a urinalysis strip from the cartridge into the toilet bowl to collect a urine sample from a urine stream delivered by the subject into the toilet bowl, retract the first end back into the housing after acquiring the urine sample and, after acquiring data, release the urinalysis strip into the toilet for disposal; and a urinalysis sensor within the housing configured to acquire data from the urinalysis strip related to the urine sample when the first end is retracted back into the housing.

In accordance with another one embodiment, a system is provided for monitoring or analyzing excreta of a subject that includes a toilet comprising a bowl and a toilet seat mounted above the bowl; and a urinalysis device including a housing on the toilet adjacent the toilet bowl, a cartridge carrying one or more urinalysis strips within the housing, a sensor for identifying when a subject begins using the toilet, an actuator configured to direct a first end of a urinalysis strip from the cartridge into the toilet bowl to collect a urine sample from a urine stream delivered by the subject into the toilet bowl, retract the first end back into the housing after acquiring the urine sample and, after acquiring data, release the urinalysis strip into the toilet for disposal, and a urinalysis sensor within the housing configured to acquire data from the urinalysis strip related to the urine sample when the first end is retracted back into the housing.

In accordance with still another embodiment, a method is provided for monitoring or analyzing excreta of a subject using a toilet that includes detecting when a subject begins using the toilet; deploying a urinalysis strip into the toilet bowl to collect a urine sample from a urine stream delivered by the subject into the toilet bowl; directing the urinalysis strip to a urinalysis sensor to acquire data from the urinalysis strip related to the urine sample; and after acquiring data, releasing the urinalysis strip into the toilet for disposal.

Other aspects and features including the need for and use of the present invention will become apparent from consideration of the following description taken in conjunction with the accompanying drawings.

BRIEF DESCRIPTION OF THE DRAWINGS

The invention is best understood from the following detailed description when read in conjunction with the accompanying drawings. It is emphasized that, according to common practice, the various features and design elements of the drawings are not to-scale. On the contrary, the dimensions of the various features and design elements are arbitrarily expanded or reduced for clarity. Included in the drawings are the following figures.

FIGS. 4A-4H show an exemplary method for completing urinalysis using the device of FIG. 2.

FIGS. 5A-5D show an exemplary method for uroflowmetry using the device of FIG. 2.

FIGS. 6A-6E show an exemplary method for stool analysis using the device of FIG. 2.

FIG. 7 is a graph showing an example of pressure detection to indicate a subject using a toilet and timing of defection.

FIGS. 8A and 8B are perspective and top views, respectively, showing an example of a dual-camera uroflowmetry module that may be included in the device of FIG. 2.

FIG. 8C shows an example of 2.5D image reconstruction based on images from each of the cameras in FIGS. 8A and 8B.

FIG. 10 is a perspective view showing an example of a fingerprint reader that can replace a conventional handle or lever on a toilet.

FIG. 10A is a detail showing a finger contacting the fingerprint reader of FIG. 10 to acquire a fingerprint when the toilet is being flushed.

FIGS. 11A and 11B show an exemplary method for acquiring an anal scan of a subject using a toilet including the device of FIG. 2.

FIG. 14 is a table showing the Bristol Stool Form Scale.

DETAILED DESCRIPTION OF THE EXEMPLARY EMBODIMENTS

Before the exemplary embodiments are described, it is to be understood that the invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described.

It must be noted that as used herein and in the appended claims, the singular forms "a," "an," and "the" include plural referents unless the context clearly dictates otherwise. Thus, for example, reference to "a compound" includes a plurality of such compounds and reference to "the polymer" includes reference to one or more polymers and equivalents thereof known to those skilled in the art, and so forth.

Figure 1:
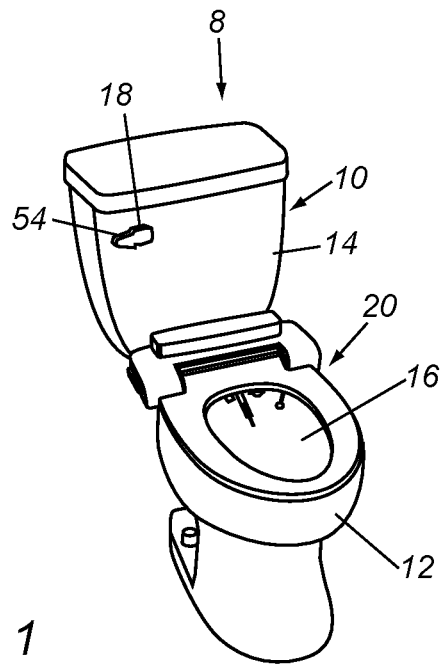
FIG. 1 is a perspective view of an exemplary embodiment of a toilet including a device mounted thereto for monitoring the excreta of a subject using the toilet.

Turning the drawings, FIG. 1 shows an example of a system 8 for monitoring and/or analyzing excreta of a subject that includes a toilet 10 including a bowl 12 and a tank 14, similar to conventional toilets, and a device 20 for monitoring and/or analyzing excreta of a subject using the toilet 10. The device 20 generally includes a housing 22 containing or carrying various components that may be mounted to the toilet 10, e.g., at the back of the bowl 12 adjacent the tank 14, and a toilet seat 24 that is positioned above and/or around the bowl 12 when the housing 22 is mounted to the toilet 10. The seat 24 may be pivotally mounted to the housing 22, e.g., by a hinge (not shown), such that the seat 24 may be raised and lowered similar to conventional toilet seats when the housing 22 is secured to the toilet 10. Thus, the device 20 may be removably mounted to a toilet 10 by simply replacing a conventional toilet seat (not shown) and enabling the various functions described herein to be performed. Alternatively, the device may be integrated into the toilet permanently, e.g., providing a custom-designed toilet including one or more integral sensors, cameras, processors, and the like, as described in elsewhere herein.

Figure 2:
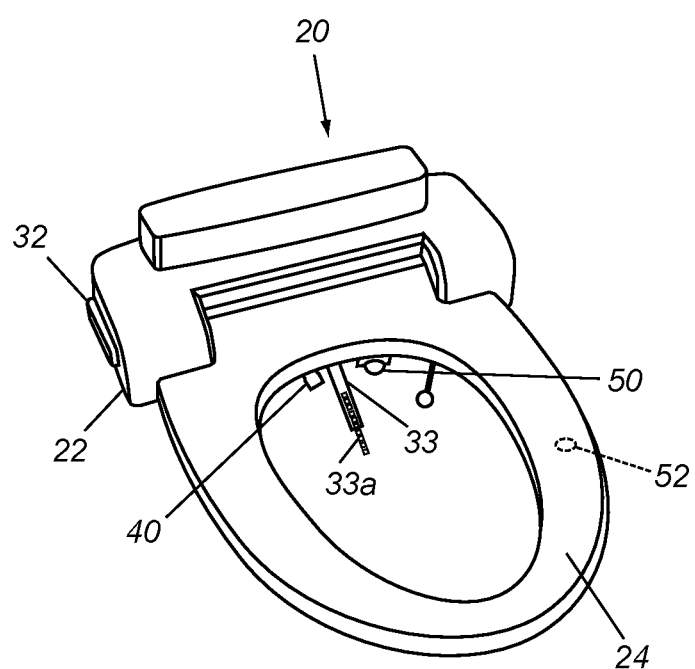
FIG. 2 is a perspective view of the device of FIG. 1 including a toilet seat and components for monitoring excreta of a subject.
Figure 3:
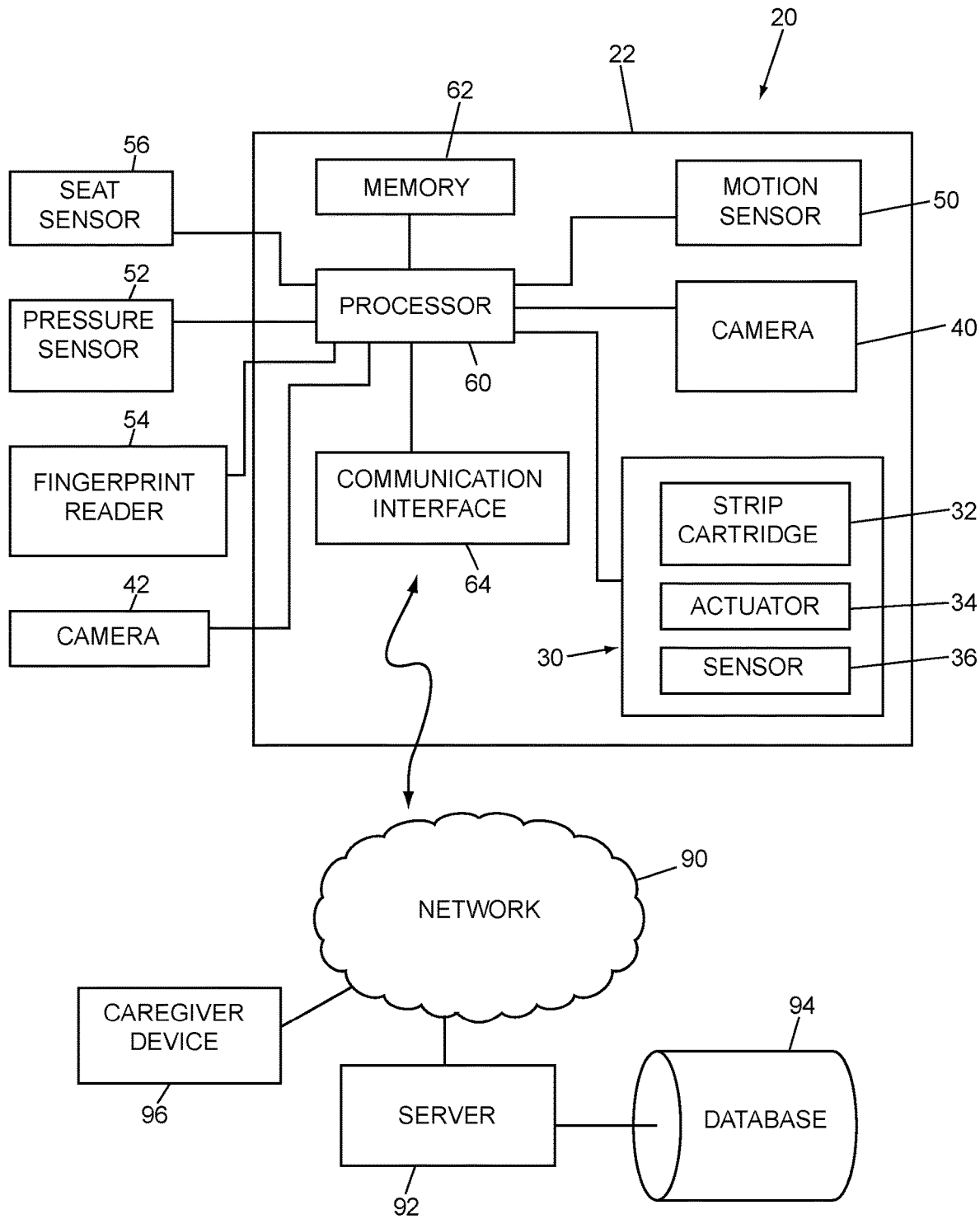
FIG. 3 is a schematic showing components of the device of FIG. 2 communicating via a network with a remote server and caregiver device.

With additional reference to FIGS. 2 and 3, the device 20 generally includes a urinalysis module 30 carried by the housing 22 that includes a cartridge 32 including one or more urinalysis strips (one strip 33 shown deployed in FIG. 2), an actuator 34 configured to deploy, retract, and/or dispose of the urinalysis strips, e.g., successively from the cartridge 32, and a sensor 36 to acquire data from the urinalysis strips after collecting urine samples, e.g., when the urinalysis strips are deployed within the toilet bowl 12, as described further elsewhere herein. For example, the actuator 34 may include one or more stepper motors, air pumps, feeders, and/or other motorized mechanisms that may be direct a urinalysis strip 33 from the cartridge 32 to deploy a first end 33a thereof into an interior 16 of the toilet bowl 12, to collect a urine sample from a urine stream 6 delivered by a subject into the toilet bowl 12, e.g., as shown in FIGS. 4A and 4B. The actuator 34 may then retract the first end 33a back into the housing 22 after acquiring the urine sample and, after analysis, release the urinalysis strip 33 into the toilet bowl 12 for disposal, e.g., as shown in FIGS. 4C-4F, and described further elsewhere herein. For example, the actuator 34 may include an air pump (not shown) that may eject the urinalysis strip 33 from the housing 22 into the toilet bowl 12.

The housing 22 may include a slot or other recess for removably receiving the cartridge 32, e.g., such that the cartridge 32 may be removed when its urinalysis strips 33 have been depleted, and a new cartridge (not shown) may be inserted. The housing 22 and/or cartridge 32 may include one or more detects, locks, or other cooperating features (not shown) to allow insertion and removal while securing the cartridge 32 within the housing 22 during operation of the device 20.

As shown in FIGS. 1 and 2, the housing 22 may be configured to be mounted at the back of the toilet 10, e.g., adjacent the tank 14. Alternatively, the housing may be configured to be mounted at other locations and/or the urinalysis module 30 may be provided at other locations relative to the toilet bowl 12, e.g., to deploy the urinalysis strips 33 at other locations within the interior 16 of the toilet bowl 12 to ensure exposure to sufficient urine when a subject urinates into the toilet 10. For example, it may be desirable to configure the urinalysis module 30 at the front or side of the toilet bowl 12, e.g., such that urinalysis strips may be deployed into the urine streams of subjects who urinate while seated on the toilet 10.

In addition or alternatively, the device 20 may include one or more cameras mounted to the housing 22 and/or seat 24 to acquire images to perform one or more of stool analysis, uroflowmetry, anal print scans, and the like. For example, as shown in FIG. 2, camera 40 may be provided on the housing 22 (or back of the seat 24) that is oriented into the interior 16 of the toilet bowl 12 when the housing 22 is mounted to the toilet 10 to acquire images of contents within the interior 16 of the toilet bowl 12, e.g., to acquire images of a subject's stool, discarded toilet paper, and the like, as described elsewhere herein. Optionally, the camera 40 may have a sufficiently wide field of view, or an additional camera 42 may be provided on the housing 22 or seat 24 that is oriented to capture images of a subject's anus when sitting on the seat 24, e.g., to obtain anal prints to identify the subject, also as described further elsewhere herein. In an exemplary embodiment, the camera 40 may be a charge-coupled device (CCD), a complementary metal oxide semiconductor (CMOS) camera, and the like, and/or may include a light source, e.g., one or more LEDs (not shown), that emit white or other light to provide sufficient light that the camera 40 can generate images with sufficient and/or consistent contrast for analysis.

Optionally, the device 20 may include one or more sensors that indicate when a subject is about to or is using the toilet 10. For example, the device 20 may include a motion sensor 50, e.g., a passive infrared motion sensor, mounted to the housing 22 and/or seat 24, e.g., oriented towards the interior 16 of the toilet bowl 12 to detect when a subject is urinating into the toilet bowl 12, also as described elsewhere herein. For example, as shown in FIG. 4A, the sensor 50 may have a wide field of view oriented towards the interior 16 of the bowl 12 to identify a urine stream 6 being directed into the toilet bowl 12. In addition or alternatively, the device 20 may include a seat sensor 56 that identifies when the toilet seat 24 is up or down. For example, an accelerometer or other device (not shown) may be mounted to or within the seat 24 or a sensor may be coupled to the hinge of the seat 24 that provides signals indicating the orientation of the seat 24.

As shown in FIG. 3, the device 20 may include one or more additional components within the housing 22, e.g., a processor 60 for controlling operation of various components of the device 20, e.g., activating and/or otherwise operating the urinalysis module 30 and/or camera(s) 40, 42, and/or for receiving, processing, and/or analyzing data and/or images from the sensors, cameras and/or other components of the device 20. The processor 60 may include one or more microprocessors and/or other hardware/software components sufficient to perform the functions described herein. Optionally, the processor 60 may include a convolutional neural network and/or machine-learning algorithm, e.g., to enhance analysis and/or processing of images and/or other data when performing the various functions described herein.

Memory 62 may be coupled to the processor 60, e.g., for storing data and/or images from components of the device 20, for storing analytical information generated by the processor 60, for storing a database of information, e.g., biometric information of one or more subjects using the device 20, and the like, as described further elsewhere herein. Optionally, the device 20 may include a clock (not shown) coupled to the processor 60, e.g., to provide time stamps and/or other timing information related to data and/or other events identified or processed by the processor 60.

In addition, the device 20 may include a communication interface 64 coupled to the processor 60, e.g., for communicating information from the device 20 to a remote location, e.g., via a network 90 to a server 92 and/or caregiver device 96, as described elsewhere herein. For example, the interface 64 may be a wireless interface, e.g., using Bluetooth or other communication protocols, to transmit information from the device 20 via local Wi-Fi devices and/or other local network, which may relay the information via the Internet, a telecommunications network, and the like. Thus, the network 90 may include one or more of a wide area network ("WAN"), a local area network ("LAN"), an intranet, a wireless network, and/or a telephony network capable of communicating information from the device 20 via interface 64. Optionally, the interface 64 may be configured to receive information from a remote source, e.g., via the network 90, such as commands, operational updates, database updates, and the like.

The device 20 may also include one or more components external to the housing 22, e.g., at various locations on the seat 24. For example, one or more pressure sensors 52 may be provided on the seat 24, e.g., on an underside of the seat 24, e.g., near the front of the seat 24.

Consequently, when a subject sits on the seat 24, the pressure sensor(s) 52 may be compressed between the seat 24 and the toilet bowl 12, thereby subjected to pressure from the subject's weight. In an exemplary embodiment, the pressure sensor 52 may be a force sensitive resistor (FSR), e.g., with a round sensing area, whose resistance may decrease when exposed to pressure from the subject's weight, thereby generating signals that may be communicated to the processor 60. Thus, the pressure sensor(s) 52 may generate signals indicating when a subject is sitting on the toilet 10, which may be analyzed and/or otherwise used by the processor 60 to activate various components of the device 20 and/or perform various functions, as described elsewhere herein.

In addition, one or more cameras 42 may be provided on the seat 24, e.g., to acquire images of the interior 16 of the toilet 14 from different angles. For example, as shown in FIG. 5A, a camera 42 may be mounted at the front of the seat 24 and angled towards the back of the toilet bowl 12 to acquire images of a urine stream 6 being delivered into the toilet bowl 12, as described further elsewhere herein. Alternatively, as shown in FIG. 8A, a pair of cameras 142 may be mounted on the seat 24, e.g., offset from one another on sides of the sear 24, e.g., for acquiring images for multi-dimensional image reconstruction, as described elsewhere herein.

Optionally, as shown in FIG. 10, a fingerprint or other biometric identification reader 54 may be provided, e.g., mounted to or integrated into a handle or flush lever 18 of the toilet 10. As shown, the conventional flush lever of the toilet 10 may be replaced with a custom handle 18 including a recess and/or other feature for receiving the reader 54 or the reader may be integrated into the handle 18. The reader 54 may be coupled to the processor 60 of the device 20, e.g., to provide signals from the sensor 54a of the reader 54 when a subject touches the handle 18, e.g., to flush the toilet 10. For example, the reader 54 may be coupled to the processor 60 via one or more wires or other leads (e.g., extending from the handle 18 to the housing 22) or via a wireless interface that communicates with the communication interface 64. In this manner, the subject using the toilet 10 may be identified, e.g., to associate data from the device 20 with the identified subject, as described elsewhere herein.

Optionally, the device 20 may include one or more additional sensors. For example, a volatile organic compound sensor (not shown) may be provided, e.g., mounted to the housing 22 or seat 24, which may be used by the processor 60 to identify the presence of volatile organic compounds, e.g., in a subject's stool, as described elsewhere herein.

Figure 12:
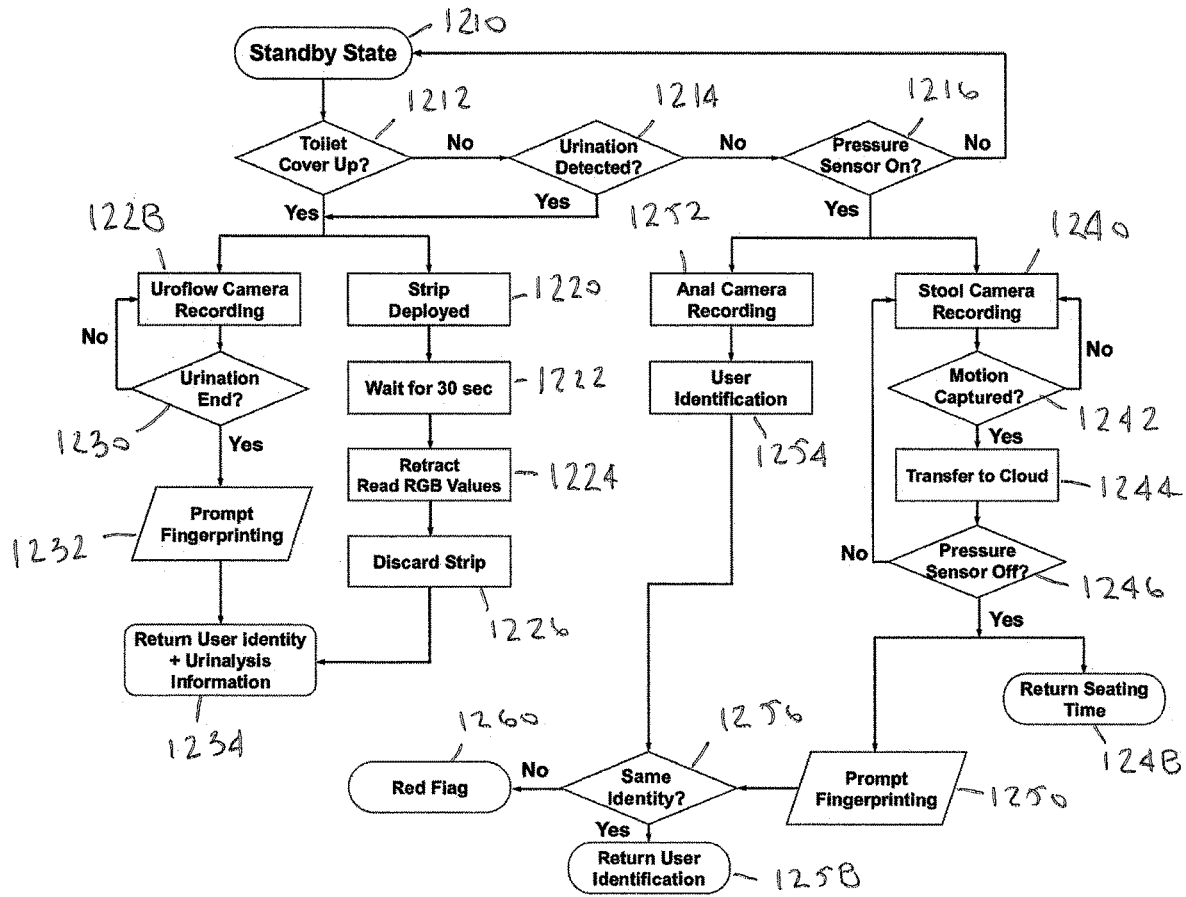
FIG. 12 is a flow chart showing an exemplary method for urinalysis.
Figure 13:
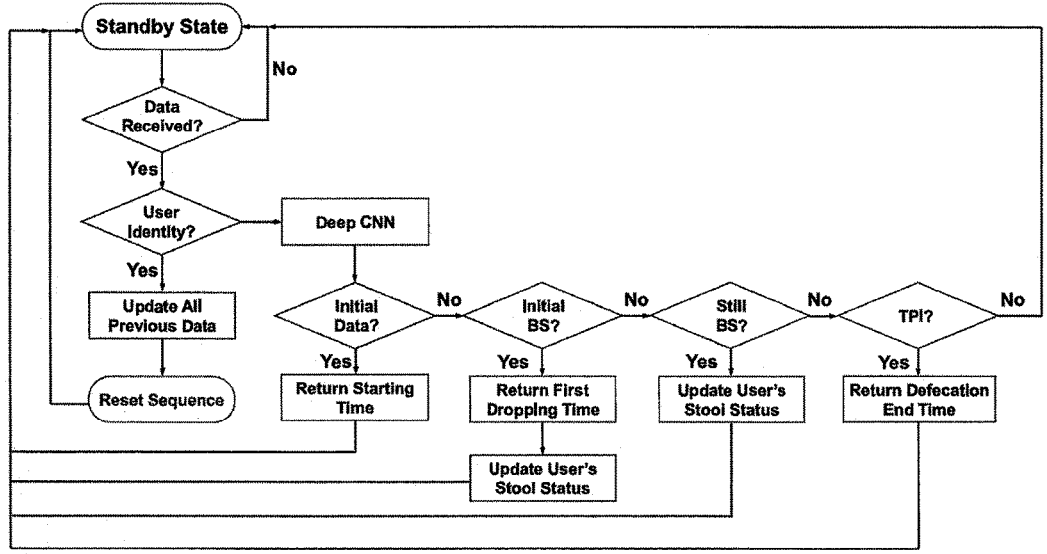
FIG. 13 is a flow chart showing an exemplary method for communicating, processing, and/or storing data from smart toilet devices at a central server.

Turning to FIG. 12, with additional reference, to FIGS. 4A-4H, an exemplary method is shown for using a device, such as the device 20 of FIGS. 1-3, to provide substantially continuous urinalysis monitoring of a subject using the toilet 10. Initially, upon turning the device 20 on, the processor 60 may place the device 20 in a standby mode 1210 and periodically monitor one or more sensors of the device 20 to identify if and when a subject uses the toilet 10. For example, at step 1212, the processor 60 may poll signals from a seat sensor 56 to identify whether the sear 24 has been lifted. If the seat 24 is lifted, the processor 60 may activate the device 20 to perform urine analysis, e.g., urinalysis and/or uroflowmetry, of the subject's urine. If the seat 24 remains down, at step 1214, the processor 60 may poll signals from the motion sensor 50 to determine whether a urine stream is detected being delivered into the toilet bowl 12. If so, again, the processor 60 may activate the device 20 to perform analysis of the subject's urine. If not, at step 1216, the processor 60 may poll the pressure sensor(s) 52 to determine whether a subject has sat on the toilet 10. If not, the processor 60 may return to the standby state 1210 for a predetermined time and then repeat polling the sensors until a change is detected. If the pressure sensor(s) 52 indicate that a subject is seated on the toilet 10, the processor 60 may activate the device 20 to perform one or more of urinalysis, stool analysis, and/or uroflowmetry.

For example, in FIG. 4A, the motion sensor 50 has detected a urine stream 6 entering the toilet bowl 12, whereupon the processor 60 activates the device 20 to perform urinalysis, as indicated by steps 1220-1234 in FIG. 12. At step 1220, a urinalysis strip 33 may be deployed into the interior 16 of the toilet bowl 12, as shown in FIG. 4B, e.g., such that the urine stream contacts the strip 33 and reacts with one or more pads or reagent regions on the strip 33.

In an exemplary embodiment, the strip 33 includes a plurality of pads or reagent regions, e.g., disposed adjacent one another along the deployed end 33a of the strip 33, that may be exposed to the urine stream. For example, the urinalysis strip 33 may be a ten-parameter urinalysis test strip that provides qualitative and/or semi-quantitative urinalysis of ten biomarkers, e.g., erythrocytes, urobilinogen, bilirubin, protein, nitrite, ketones, glucose, pH, specific gravity and leukocytes. At step 1222, the strip 33 may be deployed for a predetermined time, e.g., at least about thirty seconds, to ensure an adequate urine sample is taken.

Optionally, the device 20 may provide a prompt to the subject to encourage the subject to direct the urine stream to the strip 33, e.g., to ensure proper exposure of the strip 33. For example, the device 20 may include a speaker (not shown), which may provide an audible reminder to the subject. In a further option, the processor 60 may activate the camera 40 to acquire images and confirm that the urine stream strikes the strip 33. If so, the prompt may be skipped; if not, the prompt may be provided to the subject and the processor 60 may confirm from the camera images that the subject has complied and sufficiently exposed the strip 33. If necessary, the time of deployment of the strip 33 may be adjusted to ensure sufficient exposure.

Once the urine sample is acquired, at step 1224, the urinalysis strip 33 may be retracted back into the housing 22, e.g., as shown in FIG. 4C, and a urinalysis sensor 36 may be used to acquire data from the strip 33, e.g., as shown in FIG. 4D. In an exemplary embodiment, the sensor 36 includes a camera, e.g., a charge-coupled device (CCD), a complementary metal oxide semiconductor (CMOS) camera, and the like, e.g., to provide signals corresponding to digital images that may include changes in color of one or more of the pads or reagent regions on the strip 33 based on exposure to urine, which may be analyzed and/or otherwise processed by the processor 60. For example, the processor 60 may identify changes in the pads or reagent regions from the images from the camera to provide qualitative analysis of the corresponding biomarkers, e.g., as shown in FIG. 4E. Optionally, the sensor 36 may also include a light source, e.g., one or more LEDs 36a, e.g., as shown in FIG. 4D, that emit white or other light to provide sufficient light that the camera can generate images with sufficient contrast for analysis by the processor 60.

Once the urinalysis strip 33 is analyzed, at step 1226, the strip 33 may be discarded, e.g., advanced from the housing 22 into the interior 16 of the toilet bowl 12 and released, as shown in FIG. 4F. The strip 33 may be formed from water-soluble backbone and/or other biodegradable or disposable material, e.g., such that the strip 33 may be disposed of safely in home or business toilet waste systems.

Optionally, at step 1228, when the processor 60 identifies a urine stream or that a subject is urinating, the processor 60 may activate the camera 42, e.g., as shown in FIG. 5A (or other camera), of the device 20 to monitor the urine stream and perform uroflowmetry, as described further elsewhere herein. The processor 60 may analyze the urine stream to estimate volumetric flow of the subject's urine, time to maximum urine flow, average flow rate, and/or other properties of the urine, until the processor 60 confirms from the images that the subject has finished urinating, at step 1230. In an exemplary method, the camera 40 may be operated at a relatively high frame rate, e.g., at least about 240 Hz, for capturing the falling motion of the urine stream to calculate the flow rate. The processor 60 may select a plurality of, e.g., two, regions-of-interest (ROIs) at different heights within a camera frame. The urine pixel values at each ROI may then be plotted relative to time, resulting in time-shifted plots, and the time shift may be derived through cross-correlation calculation to determine the flow rate.

Once the subject has finished urinating, e.g., based on confirmation by the processor 60 from images from the camera 40 (or other camera), at step 1232, the subject may be prompted to flush the toilet, e.g., to contact the fingerprint reader 54, as shown in FIG. 4G, such that reader 54 may acquire a fingerprint, which the processor 60 may analyze or store to identify the subject. In an exemplary embodiment, the fingerprint reader 54 may include a light or other indicator (e.g., the sensor 54a itself) that may assist prompting the subject to provide a fingerprint and flush the toilet 10. For example, the sensor 54a may initially light in a first color, e.g., red, until the subject contacts the sensor 54a and provides an appropriate fingerprint (and flushes the toilet 10), whereupon the color may change, e.g., to green, to indicate success.

In one embodiment, fingerprints of authorized users may be stored in memory 62 of the device 20, and the processor 60 may compared the fingerprint acquired by the reader with those in memory 62 to confirm the identity of the subject. Alternatively, the processor 60 may communicate the signals from the reader 54 via the interface 64 to the remote server 92, which may analyze the signals, e.g., compare the fingerprint with subjects stored in a database 94 to identify the subject. The server 92 may then communicate the identity back to the processor 60.

Alternatively, at step 1234, the urinalysis information from the strip 33 and the fingerprint from the reader 54 may be assigned together in a common record, optionally along with a time stamp, which may be stored in memory 62 and/or communicated to the server 92 and/or other device (not shown) via the network 90. Optionally, as shown in FIG. 4H, one or more images of the user's anus may be used to acquire an anal print, which may be used to identify and/or verify the identity of the subject, as described further elsewhere herein.

Turning to FIGS. 5A-5D, an exemplary method is shown for performing uroflowmetry, e.g., while the camera 40 is active during step 1228-1230 in FIG. 12. As shown in FIG. 5A, camera 42 (or other camera) is oriented such that it's field of view can be used to acquire images of urine stream 6. In one method, the processor 60 may acquire images during urination, e.g., as shown in FIG. 5C, subtract baseline images from the camera 40 without urination, e.g., as shown in FIG. 5B, to acquire an enhanced image of the urine stream 6, e.g., as shown in FIG. 5C. Based on the resulting videos (frames) and the duration of urination, the processor 60 may estimate a volume of urine excreted. For example, with the video frame rate of the camera 42 fixed, there may be a linear correlation between the number of frames and actual time recorded to calculate the total voided volume of urine by the user, e.g., using pixel information of the urine stream in each video frame.

Figure 9:
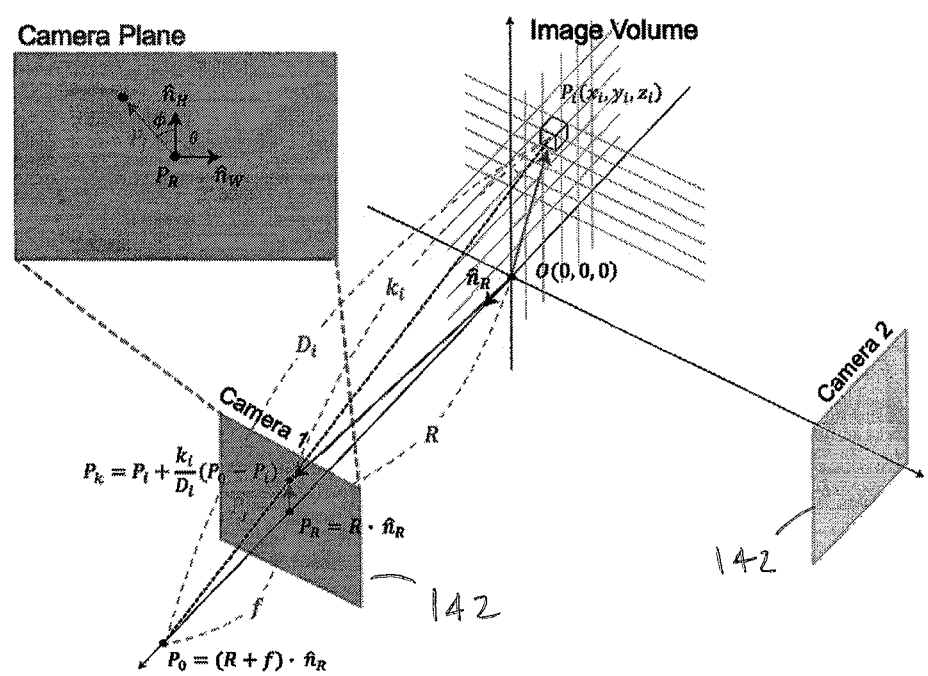
FIG. 9 shows an exemplary image reconstruction algorithm that may be performed by the module of FIGS. 8A and 8B.

Alternatively, as shown in FIGS. 8A and 8B, a pair of cameras 142 may be mounted to the housing 22 and/or toilet seat 24 such that the cameras 142 are oriented into or towards the toilet to provide multi-dimensional images of urine streams into the toilet bowl. The processor (not shown) of the device may be coupled to the cameras 142 for analyzing the images to perform uroflowmetry of individual urine streams. For example, the cameras 142 may be mounted on sides of the seat 24, offset from one another, e.g., a desired distance from the front of the sear 24, as shown in FIG. 8A, or to the housing (not shown) such that fields of views of the cameras 142 are offset substantially ninety degrees(90°) from one another and oriented such that their fields of view are centered within the same plane. As shown in FIGS. 8C and 9, the processor may analyze the resulting images to generate 2.5D images of the individual urine streams to perform the uroflowmetry, e.g., using the following methodology.

First, two camera planes are positioned in the image volume at known positions and orientations with a reference origin O(0, 0, 0). For each camera 142, there is a unit vector $\hat{n}_R$ that originates from the origin O of the image volume to the focal point of the camera, $$\hat{n}_R (n_x, n_y, n_z)$$

Here, the normal distance is defined from the origin O to the camera plane center $P_R$ as R and the normal distance from the camera plane center $P_R$ to the focal point $P_0$ as $f$. With these, the camera plane equation can be derived as below:

$$n_R \cdot (P_{cam}(x, y, z) - P_R) = 0$$

$$n_x x + n_y y + n_z z - (n_x^2 + n_y^2 + n_z^2) R = 0$$

$$n_x x + n_y y + n_z z = (n_x^2 + n_y^2 + n_x^2) R = \hat{n}_R^T \hat{n}_R R$$

Now, each voxel $P_i(x_i, y_i, z_i)$ in the image volume, $P_k$, which is the overlapped pixel between the camera plane and the $\overline{P_i P_O}$ segment, can be derived based on the following equations:

$$\hat{n}_R^T \left( P_i + \frac{K_i}{D_i}(P_0 - P_i) \right) = \hat{n}_R^T \hat{n}_R R$$

$$\frac{K_i}{D_i} = \frac{\hat{n}_R^T (\hat{n}_R R - P_i)}{\hat{n}_R^T (P_0 - P_i)}$$

$$P_k = \frac{K_i}{D_i} P_0 + \left(1 - \frac{K_i}{D_i}\right) P_i$$

From the $P_k$, $P_j$, which is the vector from the camera origin $P_R$ to $P_k$, can be acquired as below.

$$P_j = P_k - P_R$$

The pixel value of $P_j$ can then be back-projected along the line to $P_i$. For all voxels in the volume-of-interest, this back-projection image reconstruction algorithm may be performed for both cameras to reconstruct the 2.5D image of the urine stream 6, such as that shown in FIG. 8C.

Returning to FIG. 12, with additional reference to FIGS. 6A-6E, the device 20 of FIGS. 1-3 may also be used to perform stool analysis, e.g., simultaneous with or instead of urinalysis and/or uroflowmetry. Initially, at step 1216, the processor 60 may identify that a subject 4 has sat on the toilet 10, e.g., based on signals from the pressure sensor 52 on the toilet seat 24, as shown in FIG. 6A. Consequently, at step 1240, the processor 60 may activate the camera 40 (or other camera, e.g., camera 42) to acquire images of the interior 16 of the toilet bowl 12, as shown in FIG. 6B. Recording may continue until one or more events are identified by the processor 60.

For example, at step 1242, the processor 60 may poll the motion sensor 50 to identify signals indicating that the subject has excreted stool 7 into the interior 16 of the toilet bowl 12, as shown in FIG. 6C. If no motion is detected, the processor 60 may continue to acquire images from the camera 40 and, optionally, may discard earlier images to conserve memory. When motion is detected, at step 1244, the processor 60 may save images from the camera 40, e.g., including stool that has been excreted into the toilet bowl 12. The processor 60 may analyze the images to confirm that the images include stool, whereupon, the images may be stored in memory 62 and/or communicated via the interface 64 to the server 92 an/or other remote device, optionally including a time stamp. Optionally, the processor 60 may analyze the images, e.g., to classify the stool based on the Bristol Stool Form Scale (BSFS), e.g., as shown in FIG. 14, and store such classification in memory 62, or such analysis may be performed at the server 92 and stored in the database 94. In addition or alternatively, the images may be analyzed to identify the presence of blood or other matter in the stool.

At step 1246, the processor 60 may continue to periodically poll the pressure sensor 52, e.g., to confirm that the subject continues to remain seated and, if so, continue to acquire images from the camera 40, as desired. When the signals from the pressure sensor 52 indicate the subject has stood up and/or, after a predetermined time, does not resume sitting, the processor 60 may discontinue acquiring images from the camera 40 and may analyze, process, or store the images, e.g., along with a time stamp as indicated at step 1248. FIG. 7 shows an exemplary timeline of such pressure signals being polled periodically (e.g., at times $t_0$ to $t_f$) to identify that the subject 4 remains seated on the toilet 10 and respective images taken at each of the times.

Optionally, the processor 60 may identify and/or record additional parameters related to the subject, such as time to first stool ($t_2$-$t_0$ in FIG. 7), total seating time ($t_f$-$t_0$ in FIG. 7), total defecating time ($t_f$-$t_0$ in FIG. 7), and/or other parameters of the subject, which may potentially be acted on by clinicians to help manage constipation, hemorrhoids, and/or other conditions. In addition, if desired, the device 20 may provide one or more outputs to the subject, e.g., emitting an alarm or other signal if the total defecating time ($t_f$-$t_n$ in FIG. 7) exceeds a predetermined threshold, e.g., about three minutes. In another option, the processor 60 may acquire and/or analyze images from the camera 40 to estimate volume of stool excretion, e.g., similar to the uroflowmetry methods described elsewhere herein. Optionally, if a volatile organic compound sensor may be provided, the processor 60 may acquire signals from the sensor to identify the presence of volatile organic compounds in the subject's stool.

In addition or alternatively, the processor 60 may continue to acquire images of the interior 16 of the bowl 12 after confirming the subject has stood, e.g., using the camera 40 or other camera, to perform additional data acquisition and/or analysis. For example, in one embodiment, the processor 60 may acquire additional images to identify discarded toilet paper (not shown) within the toilet bowl 12. When toilet paper is identified, the processor 60 may analyze the images to identify colorimetric change of the toilet paper for cancer screening and the like. Alternatively, the processor 60 may simply store the toilet paper images in memory 62 and/or communicate the images via the interface 64 to the server 92 for storage and/or analysis.

For example, in one embodiment, the subject may use specialized toilet paper, e.g., including one or more chemicals or agents, such as those used for the guaiac fecal occult blood test (gFOBT), which may react in the presence of one or more markers, e.g., cancer cells, in the subject's stool wiped on the toilet paper. Alternatively, if normal toilet paper is used, the device may include a source of analytical chemicals within the housing, e.g., a solution of hydrogen peroxide and α-guaiaconic acid, may be sprayed or otherwise delivered from the source into the interior 16, e.g., onto the discarded toilet paper to cause a colorimetric change (molecular recognition and signal transduction), which should occur within a few seconds after application of the chemicals. The processor 60 may acquire additional images that include such potential colorimetric change and store or analyze them, as described above.

Once the subject has finished defecating, e.g., based on confirmation by the processor 60, e.g., based on signals from the pressure sensor 52, at step 1250, the subject may be prompted to flush the toilet, e.g., to contact the fingerprint reader 54 and push handle 18, as shown in FIG. 6D, such that the reader 54 may acquire a fingerprint, which the processor 60 may analyze or store to identify the subject, as described above. In one embodiment, fingerprints of authorized users may be stored in memory 62 of the device 20, and the processor 60 may compare the fingerprint acquired by the reader with those in memory 62 to confirm the identity of the subject. Alternatively, the processor 60 may communicate the signals from the reader 54 via the interface 64 to the remote server 92, which may analyze the signals, e.g., compare the fingerprint with subjects stored in the database 94 to identify the subject.

Optionally, as shown in FIGS. 6E and 11A-11B, while the subject 4 seated on the toilet 10, at step 1252 (in FIG. 12), the processor 60 may activate a camera, e.g., camera 40 (or other camera) oriented upwardly within the toilet bowl 12, to acquire one or more images of the subject's anus, e.g., to obtain an anal print of the subject, such as that shown in FIG. 11B. For example, at one or more times while the subject is seated, the camera 42 may record a short video-clip of the subject's anus. In one embodiment, at step 1254, the processor 60 may compare the images with a database of images in memory 62 to identify the subject based at least in part on the images of the subject's anus. Alternatively, the images may be communicated via the interface 64 to the server 92, which may perform the analysis and communicate the identity of the subject to the processor 60. For example, a video clip of the subject's anus may be divided into frames, and then compared to a set of reference images of the user's anal print to confirm the subject's identify.

Optionally, at step 1256, the identity obtained from the anal print may be compared to the identify obtained from the fingerprint to provide confirmation of the subject's identity. For example, at step 1258, if the identity matches, the processor 60 may store and/or communicate the information along with the other data acquired during the event. If, at step 1260, the identities do not match, the processor 60 may provide an output, e.g., audible signal, to the subject of the error to provide an opportunity for the subject to correct the error, or the error may simply be stored and/or communicated by the processor 60.

Figure 15A:
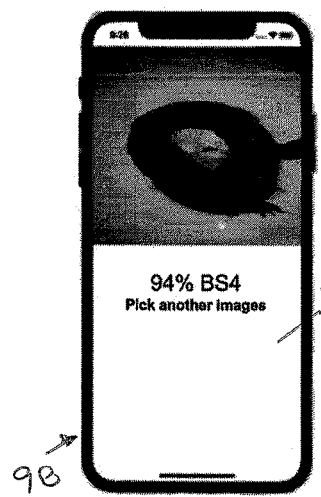
FIGS. 15A and 15B show a mobile device and an exemplary method for analyzing stool using the mobile device.
Figure 15B:
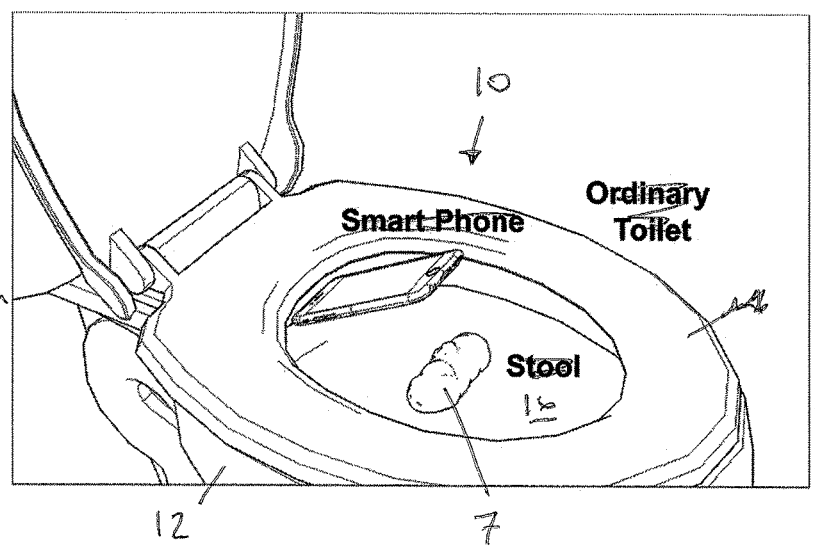

Turning to FIGS. 15A and 15B, in an alternative embodiment, a mobile electronic device 98, e.g., cellphone, tablet, and the like, may be used to acquire images to perform stool analysis and/or screening, similar to the devices herein. For example, a software application may be installed in the device 98 such a subject can acquire images of stool 7 (or discarded toilet paper) within a toilet 10 using the device's camera (rather than a camera within the toilet), as shown in FIG. 15B. The application may include a module to analyze the images and provide an output on the device's display 98a based on the analysis, e.g., as shown in FIG. 15A. Alternatively, the device 98 may communicate the images to a remote server, e.g., using a wireless or other communication interface of the device 98, and receive the resulting analysis, which may be presented on the display 98a. If the image is inadequate to perform the necessary analysis, the application may prompt the subject to acquire one or more additional images, which may then be processed and/or analyzed, similar to the methods described elsewhere herein. Such an application may allow a subject to continue to monitoring their stool while traveling or otherwise away from a location having a device 20 mounted to the toilet they regularly use.

Such stool analysis (performed using a mobile application or the smart toilet devices described herein) may be useful for monitoring and/or advising patient's having a variety of conditions. The images and resulting analysis may be used to classify the subject's stool using the BSFS, which may be used along with other criteria, such as frequency of defection and the like, to monitor conditions such as irritable bowel syndrome (IBS). For example, the Rome IV criteria make use of the BSFS and integrate it into guidelines used by clinicians around the world. The devices and methods herein may be useful for gaining information regarding a patient's number and frequency of bowel movements in order to further understand the patient's IBS. For example, bias may be present in a patient's recollection of their bowel movements, and diligently and objectively classifying stool after each and all bowel movements may be burdensome and unrealistic, especially for elderly and infirm patients. In addition, BSFS and/or other information acquired using the devices herein may be used to evaluate the response to anti-diarrheal medications such as loperamide or senna and other medications and therapies (e.g., cholestyramine), to guide the management of diarrhea during chemotherapy, and the like. It will be appreciated that the devices herein may facilitate monitoring and screening subjects for a variety of diseases and/or conditions such as those identified in the provisional applications whose contents are incorporated by reference herein.

It will be appreciated that the data, images, and/or other information acquired and/or analyzed by the devices herein may be communicated to a central server 92, e.g., for further analysis to facilitate monitoring and/or treating a plurality of patients using the devices. Optionally, if the devices identify events requiring action, the devices may communicate with the subject's caregiver, e.g., doctor, family, hospital, and the like (represented by caregiver device 96 in FIG. 3), who may take action based on the communications. For example, the devices herein may be installed in subject's homes, residential facilities, and the like for use during their regular routines. In addition, the devices may be installed in hospitals, nursing homes, and the like to facilitate monitoring patients and providing a substantially continuous monitoring and/or analysis of excreted waste from the patients, e.g., to establish health baselines and/or monitor trends or changes, which may improve treatment of the patients.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A device for monitoring or analyzing excreta of a subject using a toilet including a toilet bowl, comprising:
 a toilet seat including one or more sensors;
 a camera oriented towards an interior of the toilet bowl;
 a processor coupled to the one or more sensors and the camera and configured to:
  analyze signals from the one or more sensors to identify when a subject sits on the toilet seat;
  when the processor identifies that a subject sits on the toilet seat, activate the camera to obtain an anal print to identify the subject and obtain a set of images of contents in the interior of the toilet bowl, wherein each image in the set of images is obtained at a unique time point,
  classify each image in the set of images for toilet bowl status, wherein toilet bowl status is selected from: clean, urine, stool, and toilet paper; and
  determine at least one of total defecating time, time to first defection, and total seating time based on the time associated with each toilet bowl status.

2. The device of claim 1, further comprising:
 a fingerprint reader configured to be coupled to a flush handle of the toilet; and
 the processor coupled to the fingerprint reader for analyzing signals from the fingerprint reader to further identify the subject, wherein the processor is further configured to compare the identity corresponding to the anal print with the identity corresponding to the fingerprint to confirm the identity of the subject.

3. The device of claim 1, wherein the camera is mounted on the toilet seat such that a field of view of the camera is oriented towards a subject's anus when the subject sits on the toilet seat.

4. The device of claim 1, wherein the processor is configured to compare the images with a database of images to identify the subject based at least in part on the images of the subject's anus to obtain the anal print.

5. The device of claim 1, further comprising a stool analysis module comprising a second camera mounted such that the second camera is oriented into an interior of the toilet bowl, the processor coupled to the second camera for acquiring images of contents of the toilet bowl to analyze the subject's stool.

6. The device of claim 5, wherein the stool analysis module further comprises a processor coupled to the second camera for analyzing the images to identify discarded toilet paper within the toilet bowl and, when toilet paper is identified, analyze the images to identify colorimetric change of the toilet paper for cancer screening.

7. The device of claim 6, further comprising:
a source of cancer analytical agents; and
a processor coupled to the camera for analyzing the images to identify discarded toilet paper within the toilet bowl, the processor further configured such that, when toilet paper is identified, the source is activated to deliver the agents into the toilet bowl onto the toilet paper, the processor configured to analyze subsequent images to identify colorimetric change of the toilet paper for cancer screening.

8. The device of claim 1, further comprising a uroflowmetry module comprising a second camera mounted such that the second camera is oriented into the toilet bowl to provide images of urine streams into the toilet bowl, the processor coupled to the second camera for analyzing the images to determine one or both of flow rate and total volume of urine delivered into the toilet bowl.

9. The device of claim 8, wherein the camera is configured to capture frames at a sufficiently high rate to capture motion of the urine streams, and wherein the processor is configured to capture pixel values from the frames to calculate flow rates of the urine streams.

10. The device of claim 1, wherein the one or more sensors comprise a pressure sensor on the toilet seat configured to provide a signal when a subject sits on the toilet seat.

11. The device of claim 1, wherein the one or more sensors comprise a motion sensor such that the motion sensor is oriented into the toilet, the motion sensor configured to provide a signal when the subject begins urinating into the toilet bowl.

12. The device of claim 1, wherein the one or more sensors comprise a seat sensor that indicates whether the toilet seat is up or down.

13. The device of claim 1, further comprising a urinalysis module further comprising:
a second camera mounted such that the second camera is oriented into the toilet adjacent the toilet bowl to provide images of urine streams into the toilet bowl; and
a processor coupled to the second camera for analyzing the images to perform uroflowmetry.

14. The device of claim 1, further comprising a urinalysis module comprising:
a pair of cameras mounted and oriented orthogonally relative to one another such that the cameras are oriented into the toilet to provide multi-dimensional images of urine streams into the toilet bowl; and
a processor coupled to the cameras for analyzing the images to perform uroflowmetry of individual urine streams.

15. The device of claim 14, wherein the cameras are mounted such that fields of views of the cameras are offset substantially ninety degrees) (90°) from one another and oriented such that their fields of view are centered within the same plane.

16. A device for monitoring or analyzing excreta of a subject using a toilet including a toilet bowl, comprising:
a toilet seat including one or more sensors;
a first camera mounted such that the camera is oriented towards the anus of a subject sitting on the toilet and configured to acquire images of the anus;
a second camera mounted such that the second camera is oriented into an interior of the toilet bowl and configured to acquire a set of images of contents in the interior of the toilet bowl; and
a processor coupled to the one or more sensors, the first camera, and the second camera, wherein the processor is configured to:
analyze signals from the one or more sensors to identify when a subject sits on the toilet seat;
when the processor identifies that a subject sits on the toilet seat, activate the camera to obtain an anal print to identify the subject and acquire a set of images of contents in the interior of the toilet bowl, wherein each image in the set of images is obtained at a unique time point;
classify each image in the set of images for toilet bowl status, wherein toilet bowl status is selected from: clean, urine, stool, and toilet paper; and
determine at least one of total defecating time, time to first defection, and total seating time based on the time associated with each toilet bowl status.

17. The device of claim 5, wherein the stool analysis module further classifies the stool according to the Bristol Stool Form Scale.

18. The device of claim 1, wherein the processor utilizes a machine learning algorithm to classify each image in the set of images.

19. The device of claim 1, wherein the processor is configured to determine a parameter of the group consisting of: color of stool, blood in excreta, and combinations thereof.

20. The device of claim 19, wherein the processor is configured to identify a health condition of the individual based on the excreta classification and the at least one parameter.

21. The device of claim 20, wherein the health condition is selected from an infection, poor nutrient absorption, cancer, inflammatory bowel disease, gallstones, bile acid metabolism, estrogen metabolism, constipation, and diarrhea.

22. The device of claim 19, wherein the health condition is identified based on excreta classification and parameter determination of multiple bowel movements of the subject.

* * * * *